(12) United States Patent
Kana et al.

(10) Patent No.: US 6,613,092 B1
(45) Date of Patent: Sep. 2, 2003

(54) STEM TAPER ADAPTER

(75) Inventors: Richard J. Kana, Lexington, TX (US);
Richard J. Taft, Austin, TX (US)

(73) Assignee: Centerpulse Orthopedics Inc., Austin, TX (US)

(*) Notice: Subject to any disclaimer, the term of this patent is extended or adjusted under 35 U.S.C. 154(b) by 141 days.

(21) Appl. No.: 09/619,345

(22) Filed: Jul. 19, 2000

(51) Int. Cl.[7] ................................................ A61F 2/38
(52) U.S. Cl. .................... 623/20.15; 623/20.36; 623/22.42; 623/23.23; 623/23.45
(58) Field of Search .................... 623/18.11, 20.15, 623/20.25, 20.34, 20.36, 22.41, 22.42, 22.44, 22.46, 23.18, 23.22, 23.23, 23.25, 23.35, 23.34, 23.44, 23.45

(56) References Cited

U.S. PATENT DOCUMENTS 5,152,796 A * 10/1992 Slamin ..................... 623/20
5,782,921 A * 7/1998 Colleran et al. ........... 623/20

OTHER PUBLICATIONS

Finn Knee System Product Release Overview, pp. 1–29.

* cited by examiner

Primary Examiner—Bruce Snow
(74) Attorney, Agent, or Firm—Kenneth S. Barrow

(57) ABSTRACT

A prosthetic component includes an adaptor having a first end and a second end. The first end includes an elongated male tapered body. The second end includes a flange extending radially outwardly from the male tapered body and having an anti-rotational/anatomically orientation component formed therewith. The second end also includes a female tapered aperture formed therein which has an anti-rotational/anatomical orientation component formed therewith. The flange may include an elongated portion having a porous annular surface thereon.

12 Claims, 5 Drawing Sheets

STEM TAPER ADAPTER

BACKGROUND

The disclosures herein relate generally to orthopedic implants and more particularly to combining and interconnecting various femoral and tibial prosthetic components with prosthetic stems.

Resection of either the femur or tibia requires implantation of a distal or proximal component to replace the resected bone. Depending on how much bone is to be resected, an additional segment may need to be implanted along with the component. These components and segments are held to the remaining healthy bone through the use of a stem, which is inserted into the intramedullary canal of a skeletal member. There are many stem configurations available to suit anatomical and surgical needs. Because it is important to keep as much healthy bone as possible, and due to patient anatomical diversity and physician preferences, economic component versatility is of considerable importance.

Versatility is limited in that the femoral and tibial components of one product line are often incompatible with the stems of the same and/or a different product line. Currently, an adaptor and stem are incorporated into a single implant device. The adapter portion is used to attach the stem portion to the femoral and tibial components and/or segments. Using such a single piece device creates design limitations and an increased expense in manufacturing customized pieces to meet patient needs, and increases the inventory and number of parts required to be on hand.

Also, in order to include a porous coating on the adapter portion, the single device is heated to a very high temperature during the manufacturing process that may weaken the stem portion. Because of this, the single implant devices with smaller stem diameters cannot be manufactured with the porous coating without compromising the strength of the stem.

Consequently, what is needed is a universal adaptor to act as an interface between various stems and prosthetic devices, thereby allowing for more combinations of the implant devices and therefore, more versatility.

SUMMARY

One embodiment, accordingly, provides a surgical implantation device which is useful for interfacing a multitude of stem choices to mate with otherwise incompatible prosthetic devices used in femoral and tibial replacement or bone conserving surgery. To this end, a prosthetic component includes an adaptor having a first end and a second end. The first end includes an elongated male tapered body. The second end includes a flange extending radially outwardly from the male tapered body and having an anti-rotational component formed therewith. The second end also includes a female tapered aperture formed therein.

A principal advantage of this embodiment is that it allows physicians more versatility in customizing prosthetic implants so that they may meet the various needs of patient anatomy, and also decreases the cost of manufacturing customized pieces as well as the amount of product inventory required.

BRIEF DESCRIPTION OF THE DRAWING FIGURES

DETAILED DESCRIPTION

Two versions of an adaptor 10 used for connecting surgical implantation devices are generally illustrated in FIGS. 1–6, whereas FIGS. 7–10 illustrate how the adaptor is used in operation.

Figure 1:
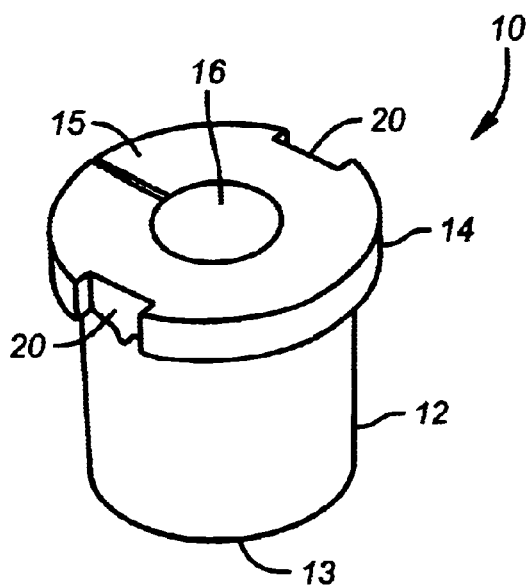
FIG. 1 is an isometric view illustrating an embodiment of a surgical implantation device used for interfacing and connecting two incompatible surgical implantation devices.
Figure 2:
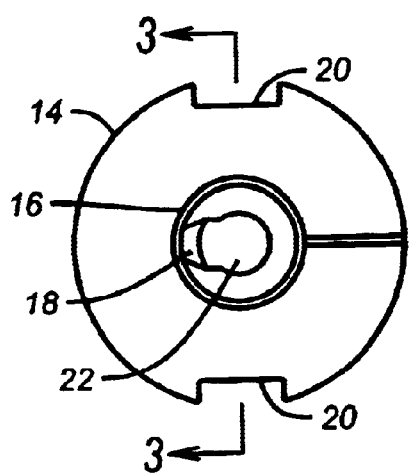
FIG. 2 is a top view of the device in FIG. 1.
Figure 3:
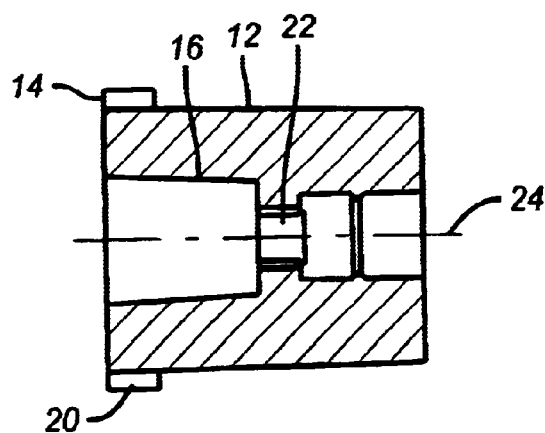
FIG. 3 is a cross-sectional view taken along the line 3—3 of FIG. 2.

The first version of the adaptor 10, FIGS. 1–3, is a device with a first end 13 and a second end 15, the first end including a male taper 12, the second end having a flange 14 with a female tapered aperture 16 formed therein and extending into the adaptor 10. An anti-rotational and orientation component such as a keyway 18 is formed in the female tapered aperture 16 and a plurality of diametrically opposed keyways 20 are formed in a peripheral surface of the flange 14 adjacent to the base of the male taper 12. The keyways 20 allow for an anti-rotational locking feature and an anatomical orientation feature used in connecting a corresponding device (discussed below). Also, an aperture 22 extends into the female tapered aperture 16 which corresponds with an aperture of a corresponding device (not shown) which is to be connected to the adaptor. Aperture 22 is aligned with a center line 24 of the adaptor 10 and allows for the corresponding device to be securely attached with a screw or the like.

Figure 4:
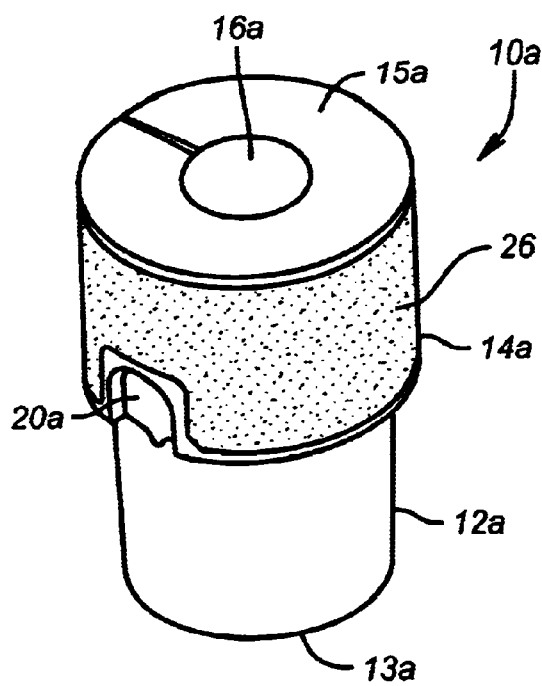
FIG. 4 is an isometric view illustrating an embodiment of a surgical implantation device used for interfacing and connecting two incompatible surgical implantation devices and for encouraging bone and tissue regrowth.
Figure 5:
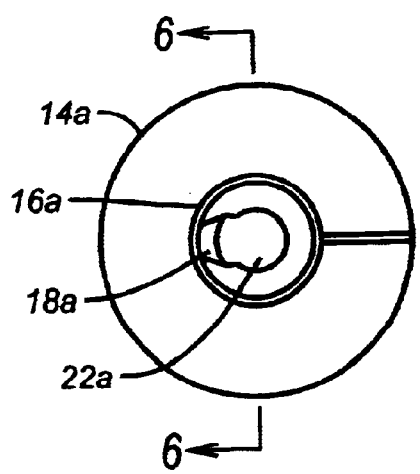
FIG. 5 is a top view of the device in FIG. 4.
Figure 6:
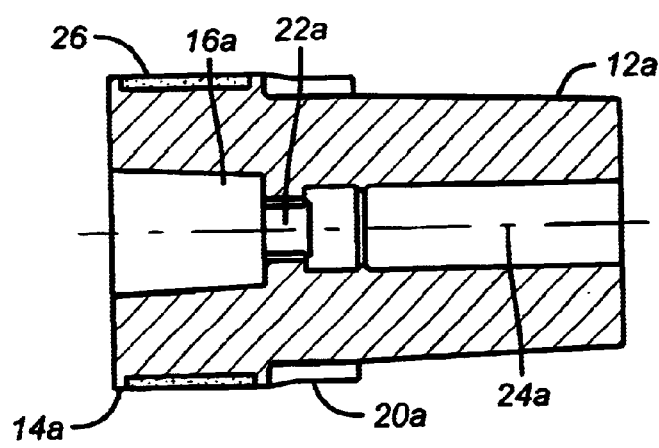
FIG. 6 is a cross-sectional view taken along the line 6—6 of FIG. 5.

The second version of the adaptor is designated 10a, FIGS. 4–6, and is substantially identical to the first adaptor 10 except that the flange 14a is elongated and includes a porous annular surface 26 so as to encourage bone and tissue regrowth. Adaptor 10a also includes first end 13a, second end 15a, male taper 12a, female aperture 16a, keyway 18a, aperture 22a and centerline 24a. However keyways 20a are formed in a portion of the flange 14a adjacent the male taper 12a and adjacent the porous annular surface 26.

Figure 7:
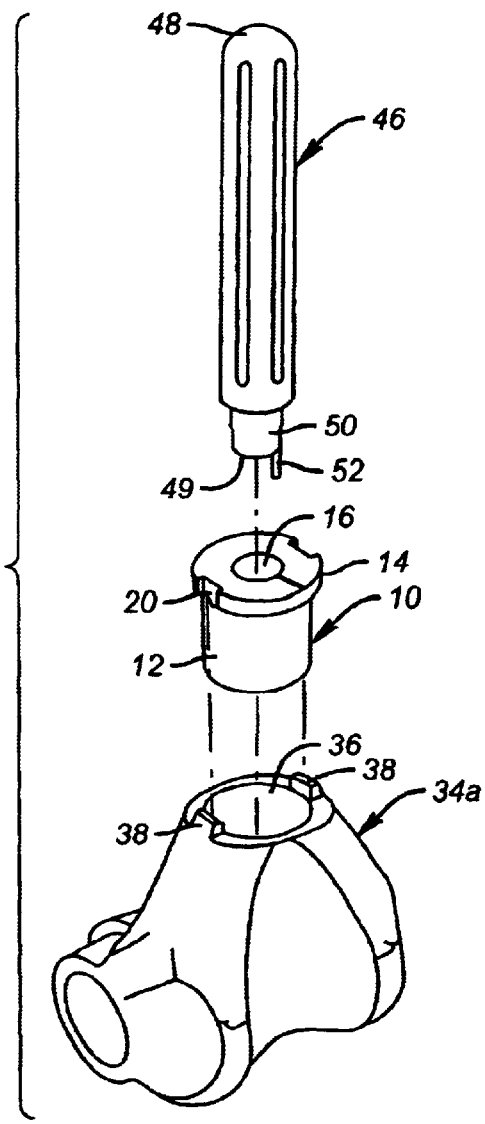
FIG. 7 is an exploded view of an embodiment of a prosthetic component, an adaptor and a stem.

In the embodiment of FIG. 7, a stem 46 includes a first end 48 and a second end 49, the first end 48 being rounded for facilitating insertion into an intramedullary canal. The second end 49 includes a male tapered portion 50 and an anti-rotational/orientation component such as a locating key 52 for engagement of stem 46 with the keyway 18 formed in adaptor 10, as discussed above.

A distal femoral component 34a includes a female tapered aperture 36 formed therein and a plurality of anti-rotational and orientation components such as diametrically opposed key members 38 projecting therefrom. The key members 38 are sized to engage the keyways 20 formed in the flange 14 of the adaptor 10 when the male tapered portion 12 of the adaptor 10 seats in the female tapered aperture 36 of component 34a. The engagement of key members 38 in keyways 20 provides a connection between femoral component 34a and adaptor 10.

Figure 8:
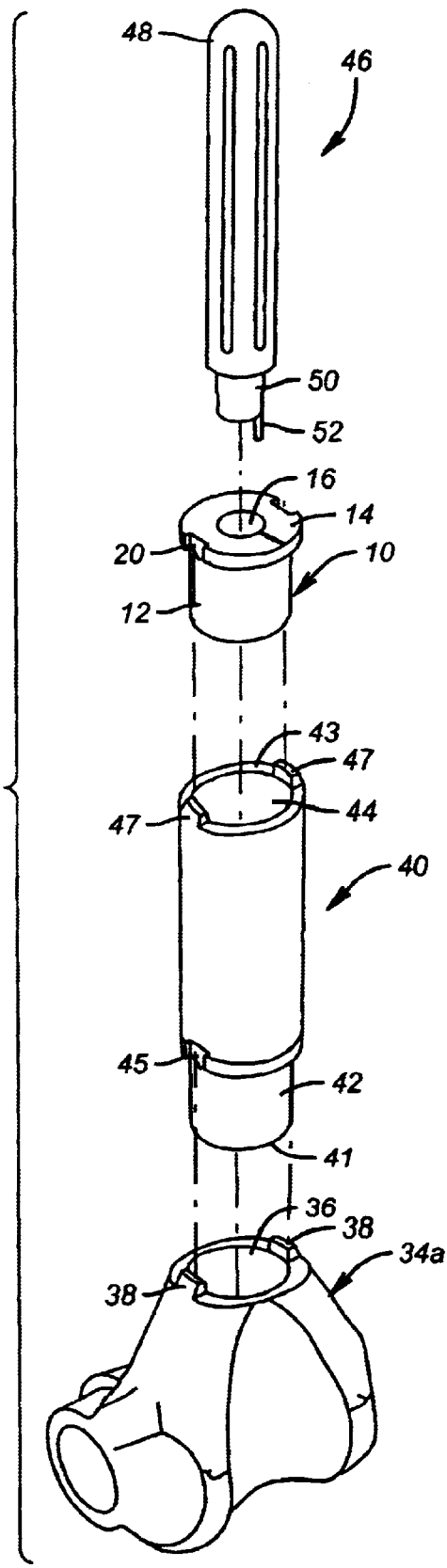
FIG. 8 is an exploded view of an embodiment of a prosthetic component, a segment, an adaptor and a stem.

In the embodiment of FIG. 8, a segment 40 is between femoral component 34a and adaptor 10. Stem 46 and adaptor 10 are connected as described above. However, the cylindrical segment 40 is interposed for connection between the adaptor 10 and the femoral component 34a. The segment 40 may be used to replace resected bone adjacent the distal femur. Segment 40 includes a first end 41 and a second end 43. The first end 41 includes a male tapered portion 42 similar to the male tapered portion 12 of adaptor 10. Thus, portion 42 seats in female aperture 36 of component 34a. A plurality of keyways 45 are formed in segment 40 for receiving the keys 38 of femoral component 34a and providing an anti-rotational/orientation connection therewith. The second end 43 of segment 40 includes a female tapered aperture 44 similar to aperture 36 of component 34a. Also, a plurality of diametrically opposed keys 47 extend from second end 43 for anti-rotational/orientation connection with keyways 20 of adaptor 10 when male tapered portion 12 is seated in female aperture 44. Also, as discussed above, the male tapered portion 50 and locating key 52 provide for engagement of stem 46 with the keyway 18 (not shown) formed in adaptor 10.

Figure 9A:
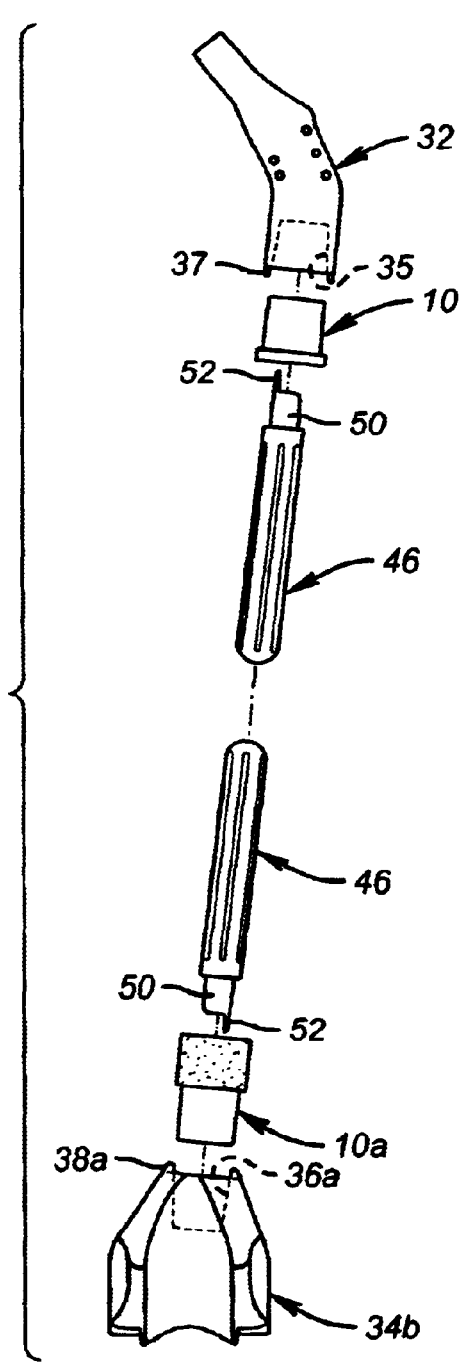
FIG. 9A is an exploded view of a combination of a proximal femoral component, an adaptor, two stems, another adaptor and a distal femoral component.

In the embodiment of FIG. 9a, a proximal femoral component 32 includes a plurality of diametrically opposed keys 37 extending therefrom and a female tapered portion 35 formed therein. Adaptor 10 seats in tapered portion 35 and keys 37 provide for anti-rotational/orientation engagement with keyways 20 (not shown) of adaptor 10. Male tapered portion 50 and locating key 52 of stem 46 engage adaptor 10 as described above. Also, a distal femoral component 34b, includes a plurality of diametrically opposed keys 38a extending therefrom and a female tapered portion 36a formed therein. Adaptor 10a seats in tapered portion 36a and keys 38a provide for anti-rotational/orientation engagement with keyways 20a (not shown) in adaptor 10a. Also, as described above, the male tapered portion 50 and locating key 52 of stem 46 provide for engagement of stem 46 with adaptor 10a.

Figure 9B:
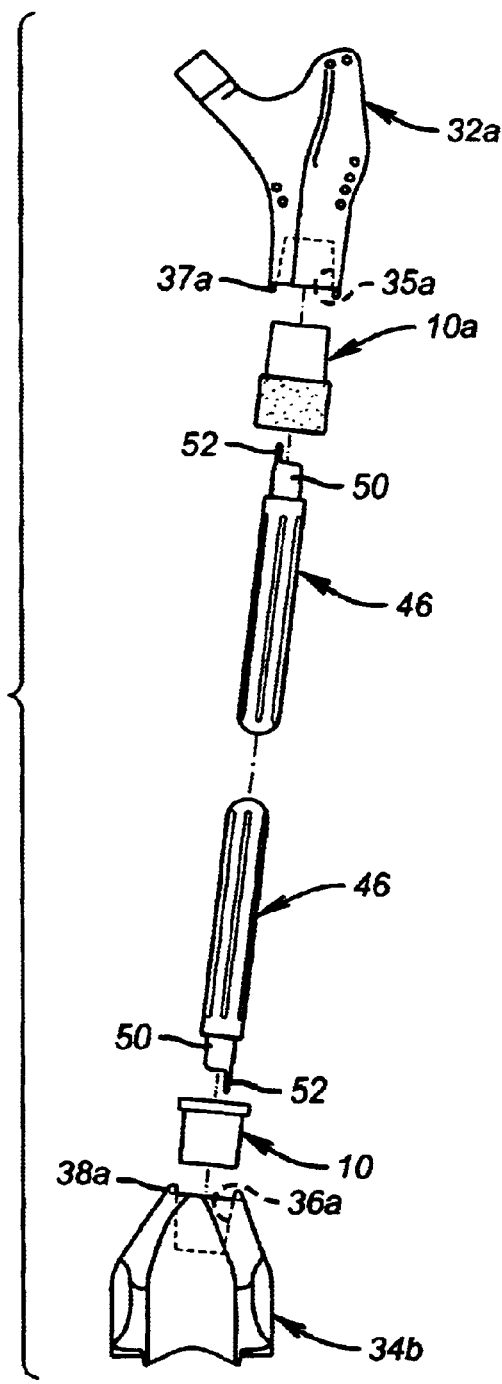
FIG. 9B is an exploded view of another combination of the devices of 9A.

In the embodiment of FIG. 9b, a proximal femoral component 32a includes a plurality of diametrically opposed keys 37a extending therefrom and a female tapered portion 35a formed therein. Adaptor 10a seats in tapered portion 35a, and keys 37a anti-rotationally engage keyways 20a (not shown) of adaptor 10a. Male tapered portion 50 and locating key 52 of stem 46 engage adaptor 10a as described above. Also, the distal femoral component 34b includes the plurality of diametrically opposed keys 38a extending therefrom and the female tapered portion 36a formed therein. Adaptor 10 seats in tapered portion 36a and keys 38a engage keyways 20 (not shown) in adaptor 10. Also, as described above, the male tapered portion 50 and locating key 52 of stem 46 provide for engagement of stem 46 with adaptor 10.

Figure 10:
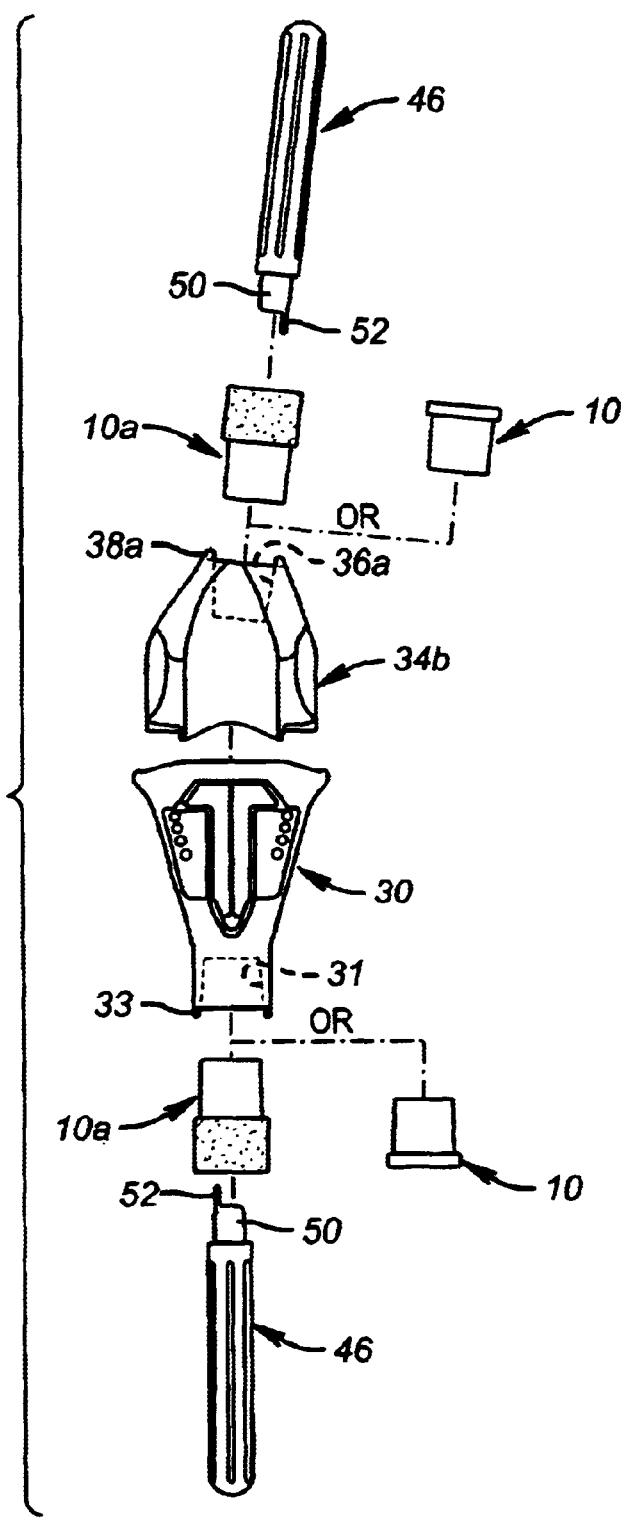
FIG. 10 is an exploded view of a stem, alternate adaptors, a distal femoral component, a proximal tibial component, additional alternate adaptors and a stem.

In the embodiment of FIG. 10, the distal femoral component 34b includes the plurality of diametrically opposed keys 38a extending therefrom and the female tapered portion 36a formed therein. Either adaptor 10 or adaptor 10a may be seated in tapered portion 36a and keys 38a engage keyways 20 (not shown) or keyways 20a (not shown), respectively. Also, as described above, the male tapered portion 50 and locating key 52 of stem 46 provide for engagement of stem 46 with either adaptor 10 or adaptor 10a. Also, a proximal tibial component 30 includes a plurality of diametrically opposed keys 31 extending therefrom and a female tapered portion 33 formed therein. Either adaptor 10 or adaptor 10a may be seated in tapered portion 33 and keys 31 engage keyways 20 (not shown) or keyways 20a (not shown), respectively. Also, as described above, the male tapered portion 50 and locating key 52 of stem 46 provide for engagement of stem 46 with either adaptor 10 or adaptor 10a.

The principal advantages of the adaptors are that they allow for varying combinations so that a physician may customize the prosthetic implant to fit patient needs. Also, to include the porous coating on only the adaptor does not require the stem to be heated to a very high temperature during the manufacturing process. Because of this, the stems are not subjected to the high temperatures and their strength is not compromised. Consequently, versatility is provided including the ability to combine devices of different systems and/or product lines. The adaptor adds such versatility by functioning as an interface between the components and stems. It should be understood that the keys and keyways may be reversed so that the result of an anti-rotational/orientation engagement between two interconnected parts is still achieved.

As a result, one embodiment provides an orthopedic implant including a prosthetic component connected to a segment used for replacing resected bone, a stem which is incompatible for connection directly to the segment, and an adaptor. The adaptor has a first end sized to connect directly to the segment and a second end sized to connect directly to the stem, thereby providing a compatible interface between the segment and the stem.

Another embodiment provides an orthopedic implant including a prosthetic component, a stem which is incompatible for connection directly to the component, and an adaptor. The adaptor has a first end sized to connect directly to the component and a second end sized to connect directly to the stem, thereby providing a compatible interface between the component and the stem.

Still another embodiment provides an orthopedic implant including a prosthetic component connected to a segment used for replacing resected bone, a stem which is incompatible for connection directly to the segment, and an adaptor which has an elongated portion including a porous annular surface. The adaptor has a first end sized to connect directly to the segment and a second end sized to connect directly to the stem, thereby providing a compatible interface between the segment and the stem.

A further embodiment provides an orthopedic implant including a prosthetic component, a stem which is incompatible for connection directly to the component, and an adaptor which has an elongated portion including a porous annular surface. The adaptor has a first end sized to connect directly to the component and a second end sized to connect directly to the stem, thereby providing a compatible interface between component and the stem.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An orthopedic implant comprising:

a prosthetic femoral component;

a segment having a first end sized to connect directly to the femoral component;

a stem incompatible for connection directly to the femoral component; and an adaptor having a first end adapted to connect directly to both the segment and the femoral component, and having a second end sized to connect directly to the stem, wherein the adaptor provides a compatible interface between the stem and the femoral component and between the stem and the segment.

2. The orthopedic implant of claim 1 wherein the segment has an elongated shape adapted to replace resected bone.

3. The orthopedic implant of claim 1 wherein the segment connects between the femoral component and stem and provides an extension to replace resected bone.

4. The orthopedic implant of claim 1 wherein the adaptor includes a first anti-rotational component to engage the stem and a second anti-rotational component to engage the femoral component.

5. The orthopedic implant of claim 4 wherein the second anti-rotational component also is adapted to engage the segment.

6. An orthopedic implant comprising:

a prosthetic femoral component;

a segment for replacing resected bone, the segment having a first end sized to connect directly to the femoral component and having a second end;

a stem, being incompatible for connection directly to the femoral component; and an adaptor having a first end sized to connect directly to both the second end of the segment and the femoral component, and having a second end sized to connect directly to the stem, wherein the adaptor provides a compatible interface between the stem and the femoral component and between the stem and the segment.

7. The implant as defined in claim 1 wherein the adaptor has an elongated portion including a porous annular surface.

8. The orthopedic implant of claim 1 wherein the segment has an elongated shape adapted to replace resected bone that is adjacent a distal femur.

9. The orthopedic implant of claim 1 wherein the first ends of the segment and adaptor have anti-rotational components, and the femoral component has an anti-rotational component that is adapted to engage both the anti-rotational component of the segment and the anti-rotational component of the adaptor.

10. The orthopedic implant of claim 9 wherein the anti-rotational components of the segment and adaptor are identical.

11. The orthopedic implant of claim 9 wherein the anti-rotational components of the adaptor, segment, and femoral component include keys and keyways.

12. The orthopedic implant of claim 1 wherein the segment has an elongated configuration that is adapted to provide an elongated extension between the femoral component and the stem; the extension being adapted to replace resected bone.

* * * * *